(12) United States Patent
Gerhardt et al.

(10) Patent No.: US 6,183,476 B1
(45) Date of Patent: Feb. 6, 2001

(54) PLATE ARRANGEMENT FOR OSTEOSYNTHESIS

(75) Inventors: Harald Gerhardt; Mevlüt Sungu, both of Rastatt; Bernhard Clasbrummel, Bochum, all of (DE)

(73) Assignee: orto Maquet GmbH & Co. KG, Rastatt (DE)

( * ) Notice: Under 35 U.S.C. 154(b), the term of this patent shall be extended for 0 days.

(21) Appl. No.: 09/344,088

(22) Filed: Jun. 25, 1999

(30) Foreign Application Priority Data

Jun. 26, 1998 (DE) .......................................... 298 11 479 U

(51) Int. Cl.$^7$ .................................................. A16B 17/80
(52) U.S. Cl. .................................................. 606/71
(58) Field of Search ................................ 606/60, 61, 69, 606/70, 71, 72

(56) References Cited

U.S. PATENT DOCUMENTS

| | | | |
|---|---|---|---|
| 3,604,414 | * 9/1971 | Borges | 606/105 |
| 4,493,317 | 1/1985 | Klaue . | |
| 5,733,287 | * 3/1998 | Tepic et al. | 606/69 |

FOREIGN PATENT DOCUMENTS

| | | |
|---|---|---|
| 335797 | 3/1959 | (CH) . |
| 566 767 | 9/1975 | (CH) . |
| 41 32 021 A1 | 4/1993 | (DE) . |
| 196 36 309 | 1/1998 | (DE) . |
| 1239266 | 12/1960 | (FR) . |
| 85 888 | 1/1986 | (LU) . |

\* cited by examiner

*Primary Examiner*—Michael Buiz
*Assistant Examiner*—David O. Reip
(74) *Attorney, Agent, or Firm*—McCormick, Paulding & Huber LLP

(57) ABSTRACT

A plate arrangement for the osteosynthesis of fractured tubular bones is made of two plate sections each connectable to associated bone sections or fragments by fastening screws passing through the plate parts. The plate parts are slidable relative to one another by means of a telescope arrangement connecting the two parts, and holes formed in the two parts for attaching the parts to bone sections or fragments are elongated in the direction perpendicular to the telescope axis to allow fastening screws to be inserted at different angles allowing the surgeon some choice in selecting a most favorable position at which to insert each screw into the associated bone fragment. The surface of each plate part facing the bone may be shaped to provide a number of small feet engageable with the bone to provide multiple point contact between the bone and the plate part, and areas of diminished cross section between pairs of adjacent screw holes allow each plate part to be bent by the surgeon on the spot to better adapt the plate to the shape of the involved bone.

7 Claims, 4 Drawing Sheets

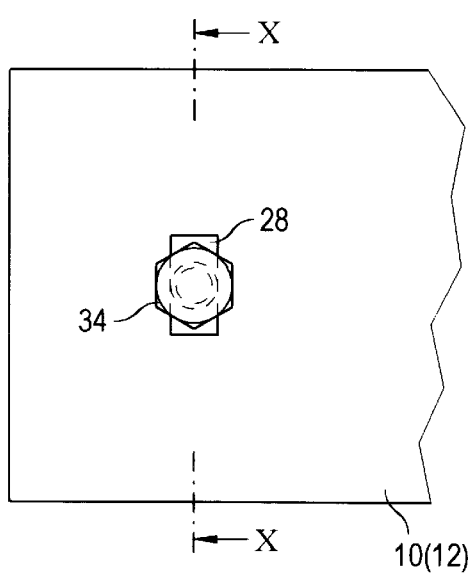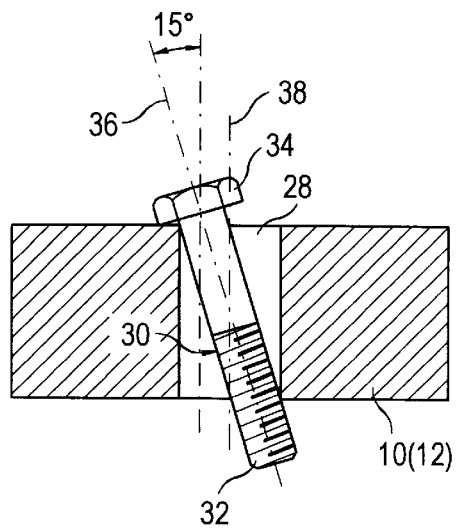
FIG.9          FIG.10
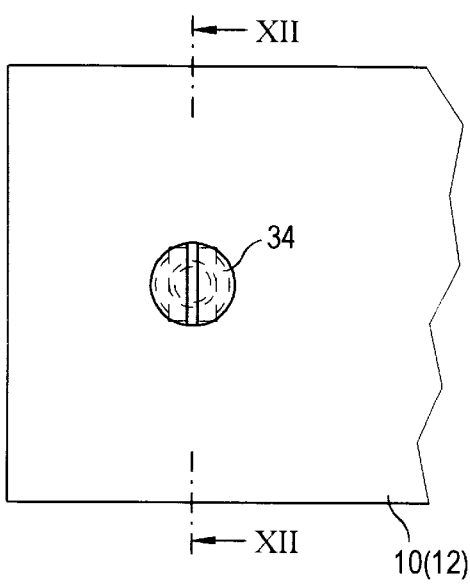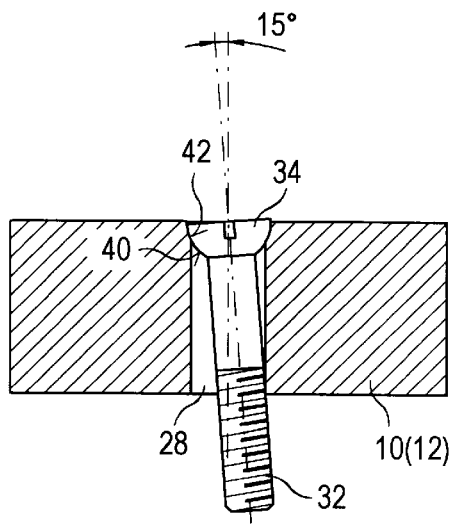
FIG.11          FIG.12 ns for osteosynthesis of fractured hollow bones by means of two plate parts, each of which is connectable by fastening screws with an associated bone section and which plate parts are connected with one another by a telescope arrangement allowing an axial relative movement of the plate parts.

BACKGROUND OF THE INVENTION

One such plate arrangement is, for example, known from DE-A-41 32 021. The axial moveability of the plate parts relative to one another allows the introduction of controlled micromovements in physiologically loaded directions so that the growth of the bone is promoted.

Since bones, such as, for example, the upper leg bones neither all have the same shape and size nor exhibit a uniform geometric form, the assembly of the plate parts to the bone fragments is not always without problems.

The invention has as its object the provision of a plate arrangement of the above-mentioned kind whereby the assembly of the plate parts to the bone sections or fragments is simplified.

SUMMARY OF THE INVENTION

The above object is solved in accordance with the invention in that the openings of the plate parts intended for the passing through of the fastening screws are formed by elongated holes, each of which has its longitudinal dimension directed perpendicular to the telescope axis.

The orientation of the elongated holes with their longitudinal dimensions perpendicular to the telescope axis assures that the introduced micromovements can be transmitted without play to the bone fragments. On the other hand, the elongated holes make possible the insertion of the screws at a given angle relative to the hole axis, so that for each screw a most favorable position in respect to fastening effect can be chosen. Moreover, the elongated holes of the plate arrangement permit a certain swivel motion about the telescope axis, and surprisingly it has been shown that a controlled amount of such swiveling movement can also have a favorable influence on bone growth.

Preferably, the longitudinal dimension of the elongated holes relative to the thickness of the associated plate parts is so chosen that the screw axis can take on an angle relative to the elongated hole axis up to about 15° to both sides of its hole axis, so that the angular displacement between the two extreme positions can amount to about 30°.

To assure a good engagement of the screw heads with the associated plate part, even if the screws are positioned inclined to the hole axis, the screw shaft near the underside of the screw head is preferably a spherical shape, with the elongated hole advantageously being surrounded by a concavely curved support surface complementary to the spherical-shaped underside of the screw head. The underside of the screw head thereby forms a kind of ball joint head which can be rotated in the support surface serving as a ball joint socket.

To give the operator the possibility to easily adapt the plate parts at the operation site to the shape of the bone in question, the plate parts in a preferred embodiment of the invention have a reduced cross section in a middle area between each two screws holes. This gives the possibility of bending the plate parts in these areas without weakening the fastening areas.

Advantageously in each of the plate surfaces facing the bone a recess is formed which extends parallel to the telescope axis. Thereby, and especially in connection with the previously mentioned cross sectional diminishment, there results on the side of each plate part intended for engagement with the bone several small feet, through which feet the plate part lies onto the bone. This enables a stable multiple point support of the plate parts on the bone.

In order on one hand to rotatably guide the plate parts relative to one another and on the other hand to improve the moveability of the plate parts relative to one another, the sections of the telescope arrangement which are inter-engageable with one another, in a preferred embodiment of the invention, are of non-circular shape, and more preferably of a polygonal cross section, so that the parts slide relative to one another by means of lands running parallel to the telescope axis. These lands can be formed on one or the other of the inter-engageable telescope sections. Thereby on one hand a secure guiding and on the other hand a reduced friction of the parts on one another is assured. Further features and advantages of the invention will be apparent from the following description which describes the invention in connection with the accompanying drawings by way of exemplary embodiments.

BRIEF DESCRIPTION OF THE DRAWINGS

The drawings are:

FIG. 9 a schematic enlarged plan view of the fastening section of a plate part with an elongated hole according to a further embodiment of the invention.

FIG. 10 a schematic cross section along line X—X of FIG. 9.

FIGS. 11 to 14 views similar to FIGS. 9 and 10 of two further embodiments of the invention.

DESCRIPTION OF THE PREFERRED EMBODIMENTS

Figure 1:
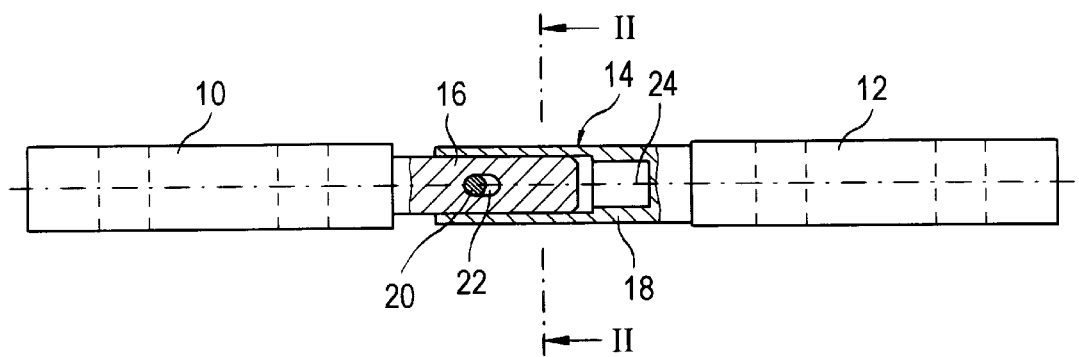
FIG. 1 a side view of a plate arrangement according to the invention.
Figure 2:
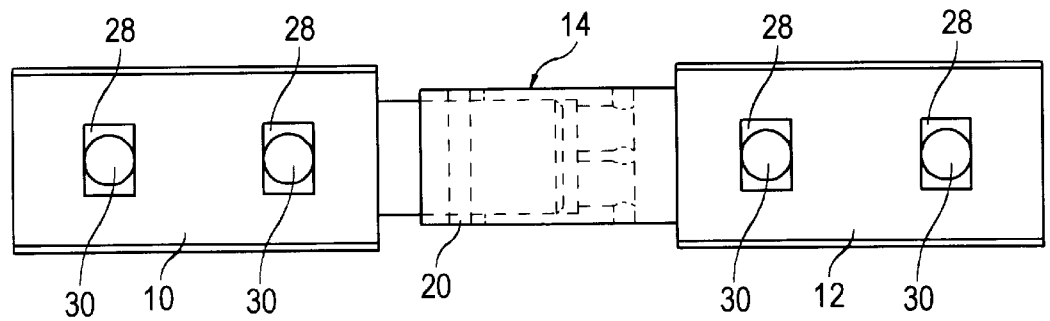
FIG. 2 a plan view of the plate arrangement of FIG. 1.

The plate arrangement illustrated in FIGS. 1 and 2 for the osteosynthesis of fractured hollow bones includes a first plate part 10 and a second plate part 12, which parts are connected with one another through a telescope arrangement or mechanism 14. The telescope mechanism includes a pin element 16 connected with the first plate part and received in a sleeve element 18 connected with the second plate part. The two plate parts 10 and 12 are secured in the assembled position by a bolt 20 which passes through the pin element 16 and which is supported in elongated holes 22 in the sleeve or guide part 18, the longitudinal dimensions of which holes run parallel to the telescope axis 24. The elongated holes 22 thereby make possible a limited movement of the plate parts 10 and 12 relative to one another in the axial direction.

Figure 3:
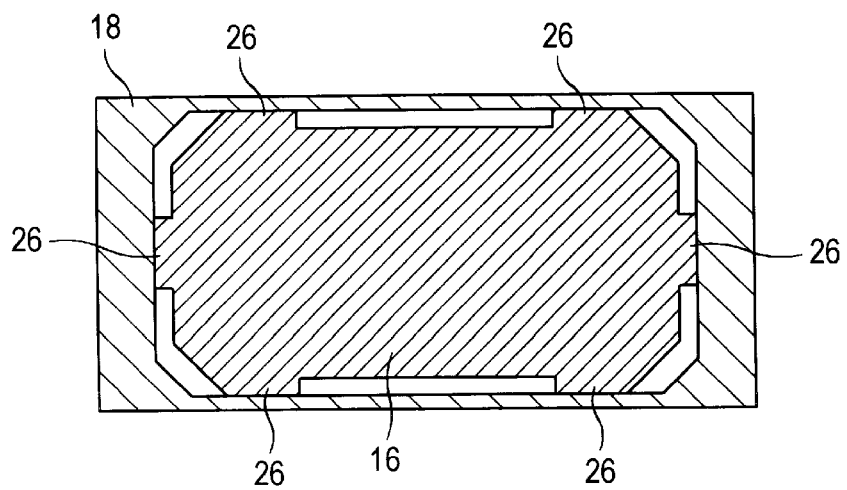
FIG. 3 a section through the plate arrangement along the line II—II of FIG. 1.
Figure 4:
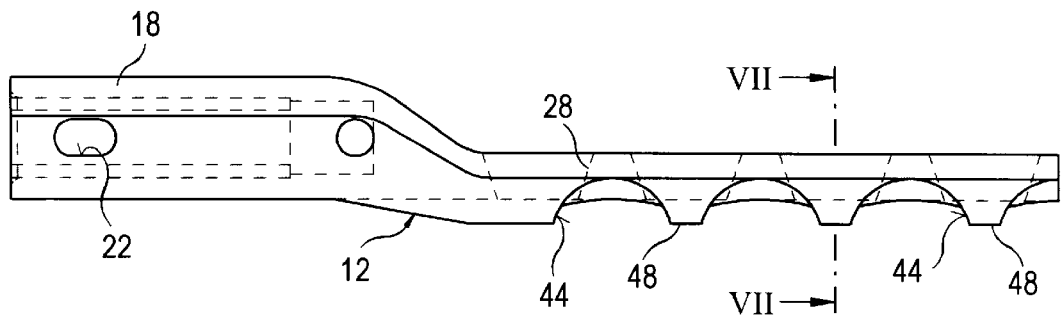
FIG. 4 a side view of a modified embodiment of a plate part.
Figure 5:
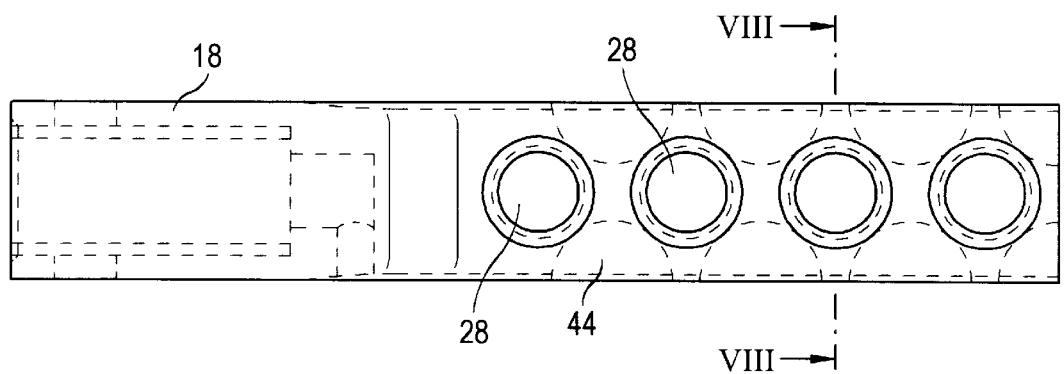
FIG. 5 a plan view of the plate part of FIG. 4.
Figure 6:
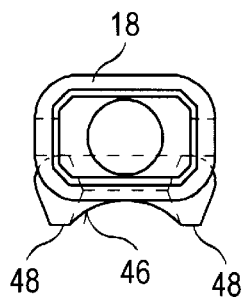
FIG. 6 a left end view of the plate part of FIGS. 4 and 5.
Figure 7:
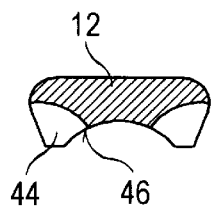
FIG. 7 a section through the plate part along the lines VII—VII of FIG. 4.
Figure 8:
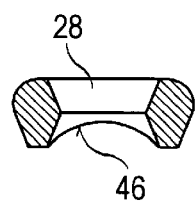
FIG. 8 a section through the plate part along the line VIII—VIII of FIG. 5.

FIG. 3 shows the cross section of the inter-engaging telescope parts 16 and 18. From this it can be seen that the pin element 16 is not full surfaced, but instead engages the walls of the guide part 18, having a polygonal cross section, only through lands 26.

According to FIG. 2, elongated hole type through passages 28 are formed in each plate part 10 and 12 for receiving fastening screws. The elongated holes or through passages 28 are arranged with their longitudinal dimension perpendicular to the telescope axis 24 so that each fastening screw 30, indicated by a circle, can move perpendicular to the telescope axis but not in the direction of the telescope axis.

FIGS. 9 to 14 show three different embodiments for the arrangement of the fastening screws in the through passages 28 with similar parts being provided with similar reference numbers.

In FIG. 10 it is seen that the screw 30 having a shaft part 32 and a screw head 34 can swing back and forth in the elongated hole 28 in the longitudinal direction of the hole, and indeed that the screw axis 36 can form an angle of ±15° with the hole axis 38. This makes possible on one hand the ability to choose a most favorable position for the driving of the screw into the bone. On the other hand, the involved plate part maintains a certain moveability with respect to the bone perpendicular to the telescope axis.

In the exemplary embodiment of FIGS. 11 and 12, the screw head 34 has a spherical or ball-shaped underside 40 which lies in a complementarily curved support surface 42, as in a ball joint socket.

Figure 13:
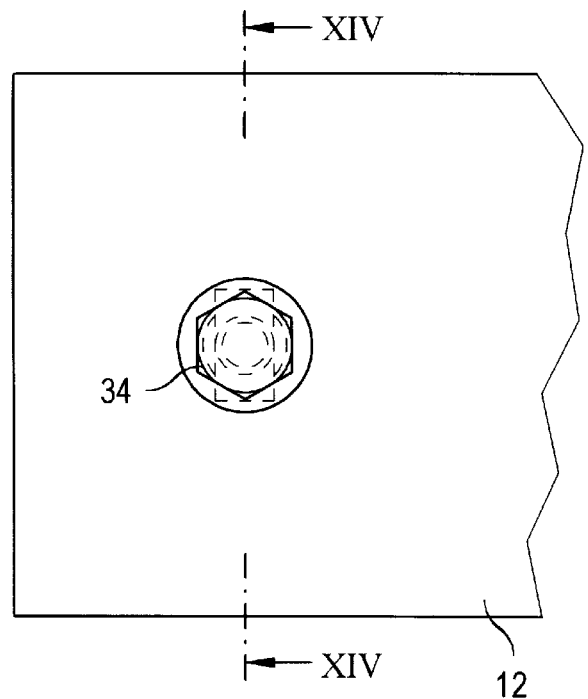
Figure 14:
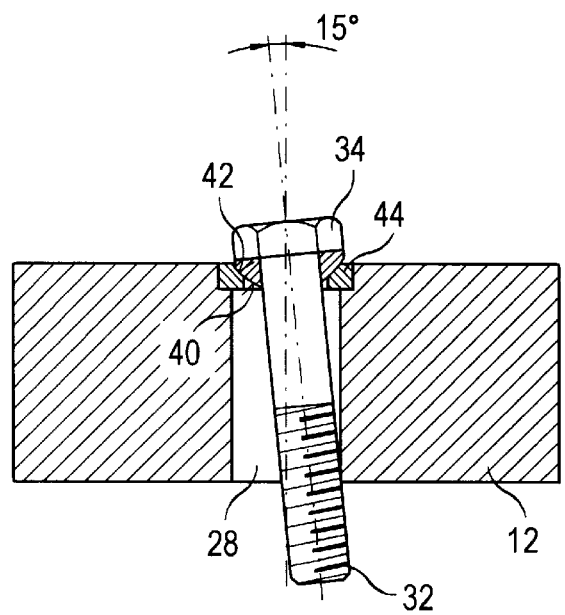

In the illustrated embodiment of FIGS. 13 and 14, the screw head has likewise a ball-shaped underside 40, with the support surface 42 being formed on a ring 44 which is inset into the through passage 28.

FIGS. 4 to 8 show a special embodiment of the second plate part 12. Similar parts are again indicated by similar reference numbers. A substantial feature of this embodiment exists in that the plate part between each two screw holes 28 has on its underside a spherically shaped recess 44 by means of which the plate cross section is reduced between each two screw holes. This gives the surgeon the possibility to bend the plate part on the spot in order to fit it better to a given bone. Further, on the underside of the plate part, that is the side of the same facing the bone, a partially cylindrical recess 46 is formed whose axis runs parallel to the telescope axis. Because of the recess 46 in combination with the recesses 44 there thereby exists laterally of the screw holes 28 small feet 48 by means of which the plate part 12 lies onto the bone at multiple points.

What is claimed is:

1. A plate arrangement for the osteosynthesis of fractured hollow bones, said plate arrangement comprising: two plate parts (10, 12) each of which is connectable to a bone section by means of a plurality of fastening screws (30) and which two plate parts are connected with one another by a telescope arrangement (16, 18) having a telescope axis (24), which telescope arrangement permits an axial movement of the plate parts (10, 12) relative to one another along the telescope axis (24), through passages (28) intended for the passing through of fastening screws (30) being formed in the plate parts (10, 12) in the form of elongated holes, each of said holes having a longitudinal dimension arranged perpendicular to the telescope axis (24).

2. A plate arrangement according to claim 1, wherein each elongated hole (28) has an axis (38), and the longitudinal dimension of each elongated hole (28) relative to the thickness of the associated plate part (10, 12) is so chosen that the screw axis (36) can take on an angle of up to about ±15° relative to the elongated hole axis (38).

3. A plate arrangement according to claim 1, wherein each fastening screw (30) has a screw shaft (32) and a screw head (34), the screw shaft (32) near the underside (40) of the screw head being of a spherical shape.

4. A plate arrangement according to claim 3, wherein each elongated hole (28) is surrounded by a concavely curved support surface (42) complementary to the spherically shaped underside (40) of the screw head (34).

5. A plate arrangement according to claim 1, wherein each plate part (10, 12) in a middle region between each two elongated holes (28) has a diminished cross section.

6. A plate arrangement according to claim 1, wherein each plate part (10, 12) has a plate surface facing the bone and having formed in it a recess extending parallel to the telescope axis (24).

7. A plate arrangement according to claim 1, wherein the telescope arrangement (16, 18) has two sections inter-engaging one another and having a non-circular cross section, and said inter-engaging sections slide relative to one another parallel to the telescope axis (24) over lands (26) extending parallel to the telescope axis (24).

* * * * *